United States Patent
Ye et al.

(10) Patent No.: US 7,993,305 B2
(45) Date of Patent: Aug. 9, 2011

(54) SPLITTABLE VALVED INTRODUCER APPARATUS

(75) Inventors: Qingshan Ye, Plymouth, MN (US); Aaron Opbroek, Brooklyn Park, MN (US)

(73) Assignee: Greatbatch Ltd., Clarence, New York ( * ) Notice: Subject to any disclaimer, the term of this patent is extended or adjusted under 35 U.S.C. 154(b) by 0 days.

(21) Appl. No.: 12/603,596

(22) Filed: Oct. 22, 2009

(65) Prior Publication Data
US 2010/0100044 A1    Apr. 22, 2010

Related U.S. Application Data

(60) Provisional application No. 61/107,447, filed on Oct. 22, 2008.

(51) Int. Cl.
*A61M 5/178*    (2006.01)
(52) U.S. Cl. ................ 604/164.05; 604/167.03
(58) Field of Classification Search ........ 604/167.01–167.06, 236–238, 604/160, 161, 164.05
See application file for complete search history.

(56) References Cited

U.S. PATENT DOCUMENTS

| | | | |
|---|---|---|---|
| 5,125,904 A | 6/1992 | Lee | |
| 5,312,355 A | 5/1994 | Lee | |
| 6,712,789 B1 | 3/2004 | Lange et al. | |
| 6,712,791 B2 * | 3/2004 | Lui et al. | 604/167.04 |
| 6,808,509 B1 * | 10/2004 | Davey | 604/167.04 |
| 7,192,433 B2 * | 3/2007 | Osypka et al. | 606/108 |
| D573,256 S | 7/2008 | Mauch | |
| 7,422,571 B2 * | 9/2008 | Schweikert et al. | 604/167.04 |
| 7,637,893 B2 * | 12/2009 | Christensen et al. | 604/167.04 |
| 7,744,571 B2 * | 6/2010 | Fisher et al. | 604/167.04 |
| 2006/0052749 A1 | 3/2006 | Moyer | |
| 2007/0123825 A1 * | 5/2007 | King et al. | 604/160 |
| 2008/0082056 A1 | 4/2008 | Mauch et al. | |
| 2009/0030374 A1 | 1/2009 | Osypka | |
| 2009/0192463 A1 * | 7/2009 | Nardeo et al. | 604/164.01 |
| 2009/0234290 A1 * | 9/2009 | Fisher et al. | 604/164.05 |

FOREIGN PATENT DOCUMENTS

| | | |
|---|---|---|
| JP | 4221575 | 8/1992 |
| WO | 9714456 | 4/1997 |
| WO | 0149363 | 7/2001 |

OTHER PUBLICATIONS

European Search Report Dated Mar. 10, 1020.
JP 4221575, Aug. 12, 1992, Susumu et al. Abstract.

* cited by examiner

*Primary Examiner* — Nicholas D Lucchesi
*Assistant Examiner* — Jenna Zhang
(74) *Attorney, Agent, or Firm* — Michael F. Scalise

(57) ABSTRACT

An improved splittable medical device introducer designed to introduce a medical device such as a lead or catheter, into a patient's vasculature without loss of blood or the introduction of air is described. The introducer assembly is designed to easily separate in a smooth tactile manner without disrupting placement of the medical device during removal of the introducer. The introducer is composed of a fluoropolymeric material which combined with an internal stress confining structure propagates a stress initiated by the operator that tears the entire introducer assembly in two without creating a jagged separated edge.

15 Claims, 10 Drawing Sheets

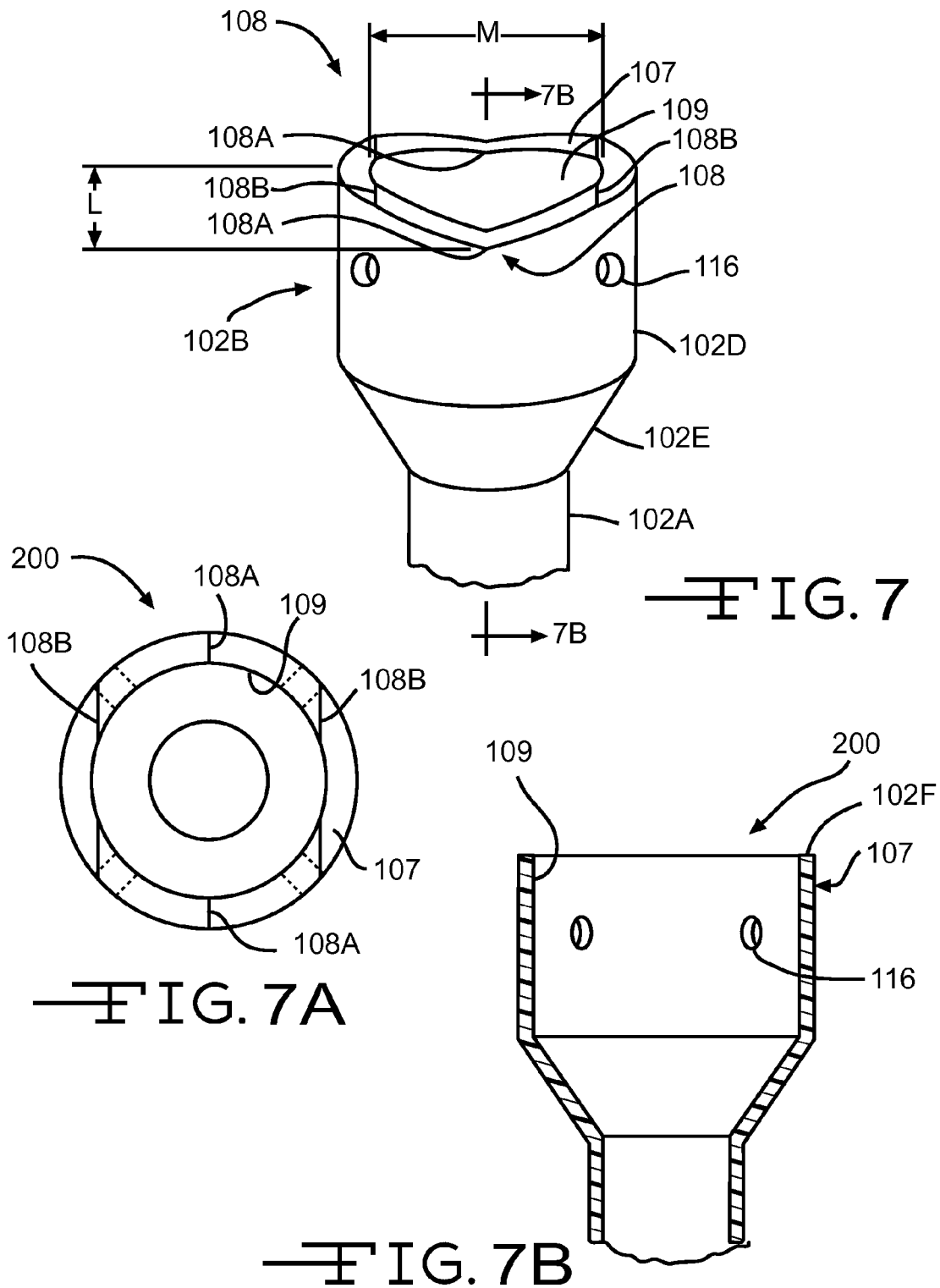

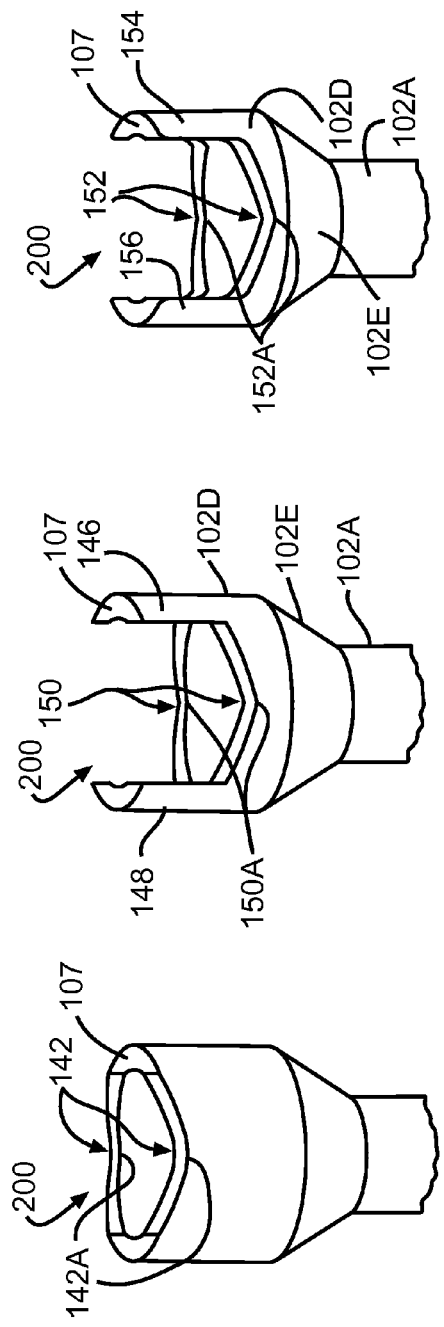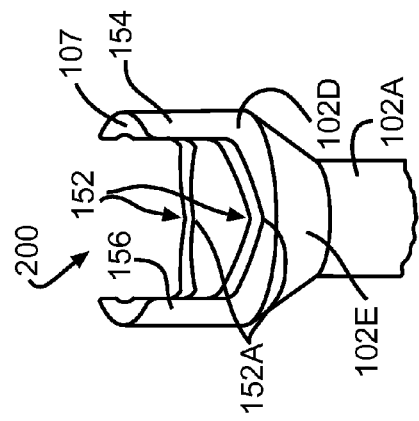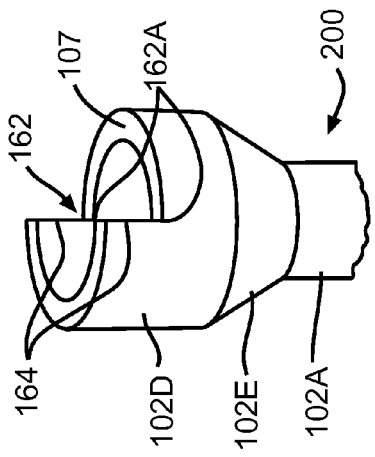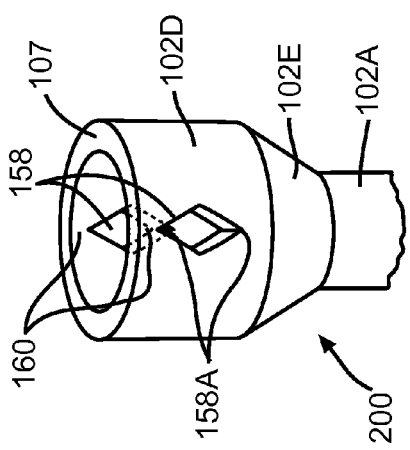

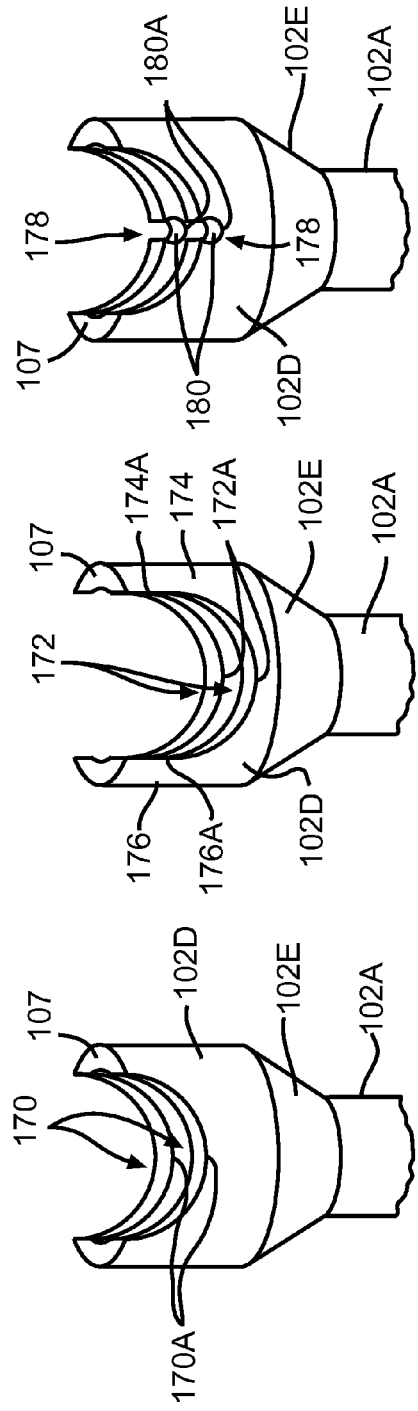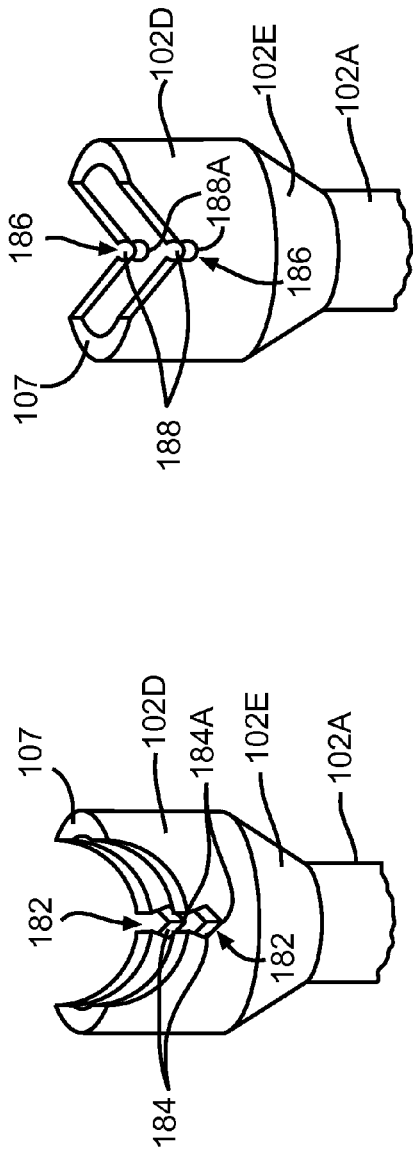

US 7,993,305 B2

SPLITTABLE VALVED INTRODUCER APPARATUS

CROSS-REFERENCE TO RELATED APPLICATION

This application claims priority from U.S. provisional Application Ser. No. 61/107,447, filed Oct. 22, 2008.

BACKGROUND OF THE INVENTION

1. Field of the Invention

The present invention generally relates to introducers and introducing assemblies. Specifically, the present invention is directed to a splittable introducer with a hemostatic valve.

2. Prior Art

Introducer devices are employed for inserting catheters, guide wires, or other medical devices into patients. A typical procedure provides for insertion of a needle into the vasculature of a patient. After insertion of the needle, a guide wire is inserted through the needle, and the needle is removed. A dilator and sheath are inserted over the guide wire, and the dilator and guide wire may be removed leaving the sheath protruding from the patient's vein. A diagnostic or therapeutic catheter (e.g. a central venous access catheter) or guide wire or other medical device, is then inserted through the sheath into the patient.

Peelable sheaths that can be peeled off of a catheter are available. Examples of these types of sheaths are shown in U.S. Pat. Nos. 5,125,904 and 5,312,355, both to Lee. As shown in FIGS. 1 and 2, the Lee patents describe a peelable or splittable valved introducer sheath assembly 10 comprising a splittable sheath 12 connected to a splittable hemostatic valve assembly 14. A sidearm 16 provides for flushing the introducer as needed. The valve assembly 14 includes a valve membrane 18 (FIG. 2) through which a lead or catheter may be introduced into a patient's vasculature without leakage. Both the sheath 12 and valve assembly 14 are splittable or have a peel-away construction that permits their removal while leaving the lead or catheter in place. This peel-away feature is made possible by a pair of longitudinal score lines 20 and 22 that have a V-shaped cross section and a depth part-way through the thickness of the respective sheath 12 and valve assembly 14. The score lines 20, 22 are positioned diametrically opposed to each other and run the entire axial length of the sheath 12 and valve assembly 14. At the end of an operation, the physician grasps the opposing flange portions 24 and 26 to peel the sheath 12 and valve assembly 14 apart as the sheath is pulled out of the vasculature, leaving the lead in place.

According to the prior art, in addition to the V-shaped groove the score line can be a linear perforation, linear slit, linear slot, linear tab, linear severing, linear weakening or linear tear that runs partially or completely along the axial length of the sheath 12 and valve assembly 14 to permit the entire length of introducer sheath 10 to be manually separated. Of course, the score line cannot be entirely through the thickness of the sheath 12 and valve assembly 14. That would create a leak and defeat the hemostatic function of the splittable introducer and valve assembly.

While not described in the Lee patents, it is know that the sheath 12 and valve assembly 14 are made of a PEBAX polymeric material. Even with the score line structure, the sheath 12 and valve assembly 14 typically experience considerable resistance to being pulled apart and separated. FIG. 2 is an illustration showing a separated valved introducer according to Lee having a "saw-tooth" edge 26. The problem is that the score lines 20, 22 provide the physician with a jerking tactile feel that makes it difficult to separate the two halves of the sheath 12 and valve assembly 14 from each other. This means that many physicians are reluctant to use the Lee valved introducer. The concern is that as the sheath and valve assembly are being separated, the jerking, sawtooth manner in which that occurs can inadvertently move the lead or catheter out of its proper position. This, of course, is completely unacceptable.

Accordingly, a valved introducer is needed that readily provides for moving a medical device, such as a lead or a dialysis catheter, into the vasculature of a patent and that is subsequently removable from the vasculature in a smooth tactile manner without disrupting placement of the medical device. The introducer must also seal around the medical device to substantially prevent blood lose there through and air embolism into the vasculature.

BRIEF DESCRIPTION OF THE DRAWINGS

FIG. 7 is a perspective view, partly broken-away, of a preferred embodiment of a stress confining structure 200 for the proximal section 102BG of the sheath 102 in the form of an inlet with diametrically opposed V-shaped inlets 108.

FIG. 7A is an enlarged overview perspective of the proximal end of the stress confining structure 200 of FIG. 7.

FIG. 7B is an enlarged cross section of the confining structure 200 along line 7B-7B of FIG. 7A FIGS. 8 to 17 illustrate alternate embodiments of stress confining structures 200 for the sheath 102 according to the present invention.

DESCRIPTION OF THE PREFERRED EMBODIMENTS

Figure 1:
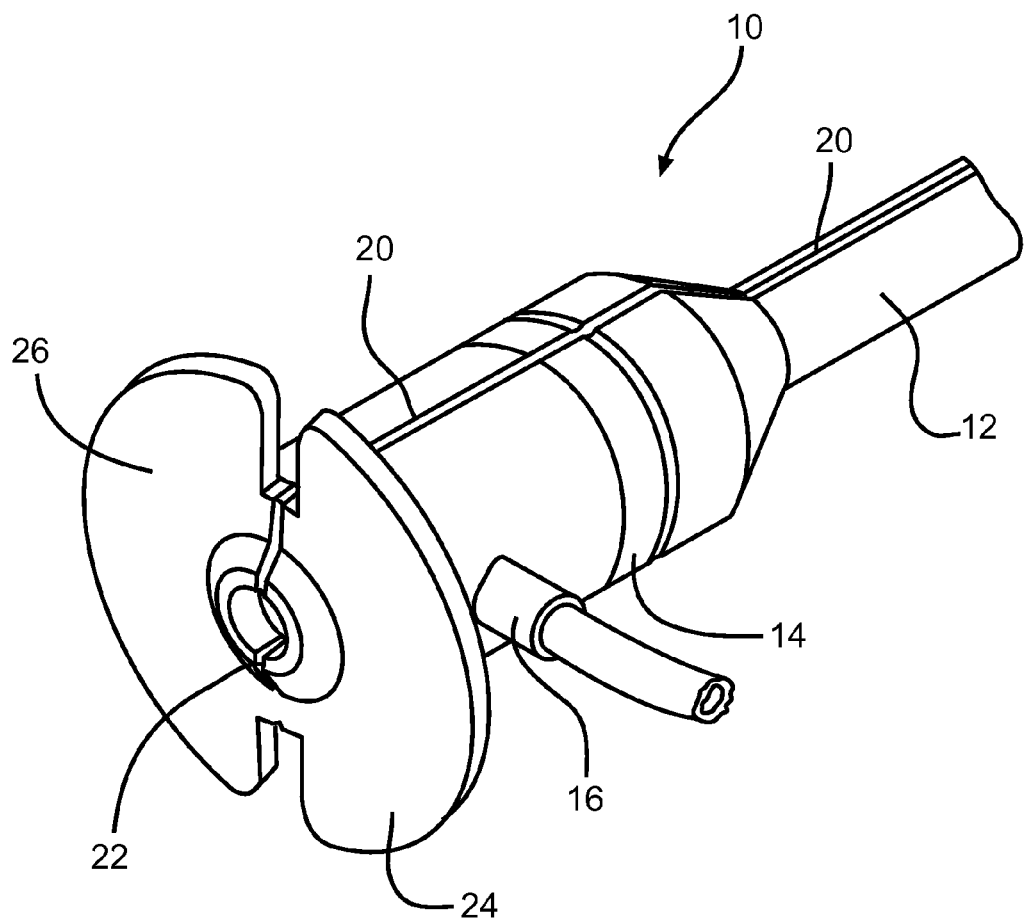
FIG. 1 is a perspective view of an introducer apparatus 10 constructed in accordance to the prior art.

FIGS. 3 to 6B illustrate one preferred embodiment of a valved introducer assembly 100 according to the present invention. The valved introducer assembly 100 comprises a sheath 102 seal connected to a valve housing 104 supporting a valve membrane 106. The sheath 102 is an elongate member having a sidewall 102A extending along a longitudinal axis 105 from a proximal section 102B to a distal end 102C. The thickness of the sidewall 102A including the proximal section 102B extending to the distal end 102C is from about 0.001 inches to about 0.050 inches A lumen or passage 110 provides for open communication along the entire length of the sheath 102 and into the valve housing 104. This lumen 110 allows for a medical device, such as a lead or catheter, to be advanced through the assembly 100. The lumen 110 preferably has a diameter from about 0.05 inches to about 0.50 inches.

The valve housing 104 comprises a lower valve body 104A and an upper cap 104B. The lower valve body 104A is over-molded onto the proximal sheath section 102B and includes spaced apart wings 112 and 114 which give the valve housing 104 a butterfly appearance.

In the preferred embodiment shown in FIGS. 3 to 6B, the proximal sheath section 102B comprises a cylindrical portion 102D leading to a frusto-conical portion 102E that extends downwardly and inwardly toward the remainder of the sheath sidewall 102A to the distal end 102C thereof. In the alternative, the proximal section 102B can have a similar diameter as the remainder of the sheath sidewall 102A.

The cylindrical sidewall portion 102D includes a stress confining structure 200 for the sheath 102 in the form of diametrically opposed circular perforations 166 (only one shown) that penetrate completely through the thickness thereof. While the perforations 166 are preferably circular, they can be of other shapes including, but not limited to, triangular, diamond-shaped, squared or star-shaped.

As will be described in detail hereinafter, the perforations 166 help propagate splitting of the sheath 102 once the valve housing 104 has been at least partially split apart. The perforations 166 have a preferred diameter ranging from about 0.01 inches to about 0.10 inches and are located relatively close to the proximal end of the cylindrical portion 102D. This distance is labeled as "X" in FIG. 6 and preferably ranges from about 0.01 inches to about 0.05 inches from the proximal end of the cylindrical portion 102D.

Figure 6:
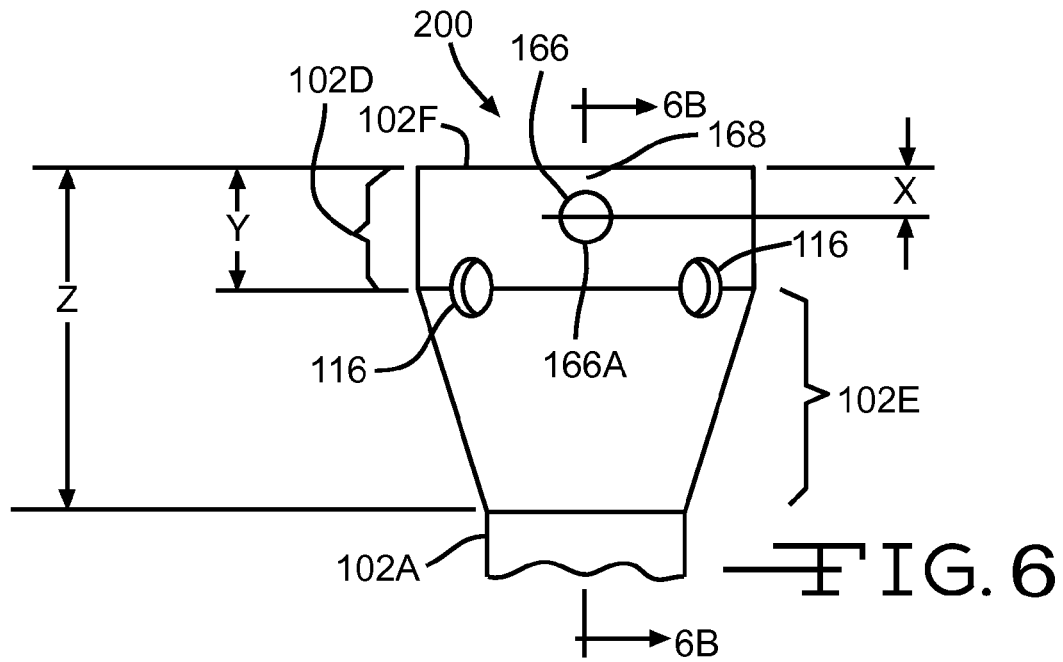
FIG. 6 is a perspective view, partly broken-away, of a preferred embodiment of a stress confining structure 200 for the proximal section 102B of the sheath 102 in the form of an inlet with a diametrically opposed circular cutout 166 and circular perforations 116.
Figure 6A:
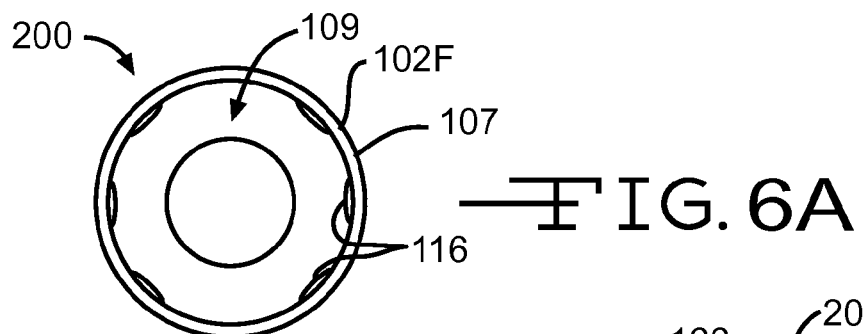
FIG. 6A is an enlarged overview perspective of the proximal end of the confining structure 200 of FIG. 6.
Figure 6B:
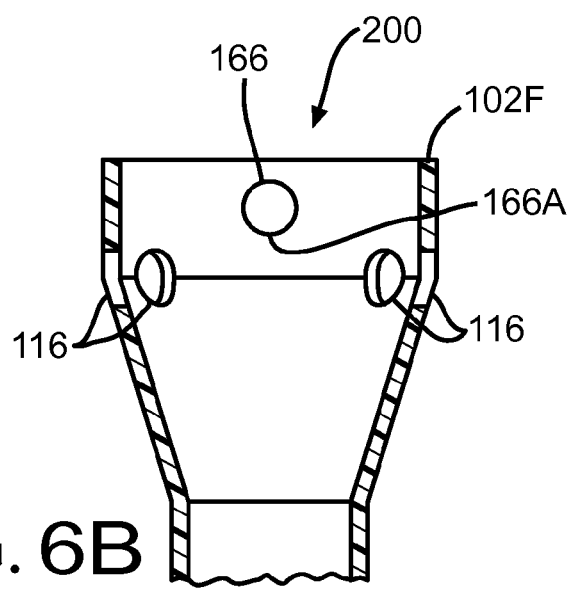
FIG. 6B is an enlarged cross section of the confining structure 200 along line 6B-6B of FIG. 6A

As particularly shown in FIGS. 6 to 6B, the proximal section 102B has a diameter ranging from about 0.01 inches to about 0.50 inches. The length of the cylindrical portion 102D labeled as "Y" in FIG. 6 is from about 0.1 inches to about 0.4 inches. The frusto-conical portion 102E has a preferred length from about 0.1 inches to about 0.6 inches. The combined length of the cylindrical portion 102D and the frusto-conical portion 102E labeled as "Z" is from about 0.2 inches to about one inch.

The cylindrical portion 102D of the proximal sheath section 102B includes a series of perforations 116 that are evenly spaced about the circumference thereof. These perforations 116 are in addition to the stress confining perforations 166 and are preferably circular with a diameter ranging from about 0.01 inches to about 0.05 inches. They are located relatively close to where the cylindrical portion 102D meets the frusto-conical portion 102E, or about 0.05 inches to about 0.3 inches from the proximal end of the cylindrical portion 102D. When the valve body 104A is over-molded onto the proximal sheath section 102B, the polymeric material of the valve body fills into these perforations 116 to lock the two together. If desired, the proximal sheath section 102B can also be surface treated to increase its rugosity and thereby enhance the sealed relationship between the valve body 104A and the sheath 102.

The valve membrane 106 is of a relatively pliable polymeric material in the form of a disc, preferably having an oval shape, provided with a central opening 118. The central opening 118 comprises an upper cylindrical portion 118A leading to a bellow portion 118B having a pleated, expansible shape which, in turn, leads to a lower cylindrical portion 118C of a diameter preferably somewhat less than the upper cylindrical portion 118A and the bellows 118B. This structure allows medical devices such as leads and catheters to easily and smoothly pass through the valve membrane 106 while preventing any substantial amount of body fluids, and particularly blood, from leaking out or any appreciable amount of ambient air from leaking in. A pair of cylindrically-shaped through holes 119 is provided through the thickness of the valve membrane 106 on opposite sides of the central opening 118. The valve membrane 106 further includes a score line 106A.

Figure 4:
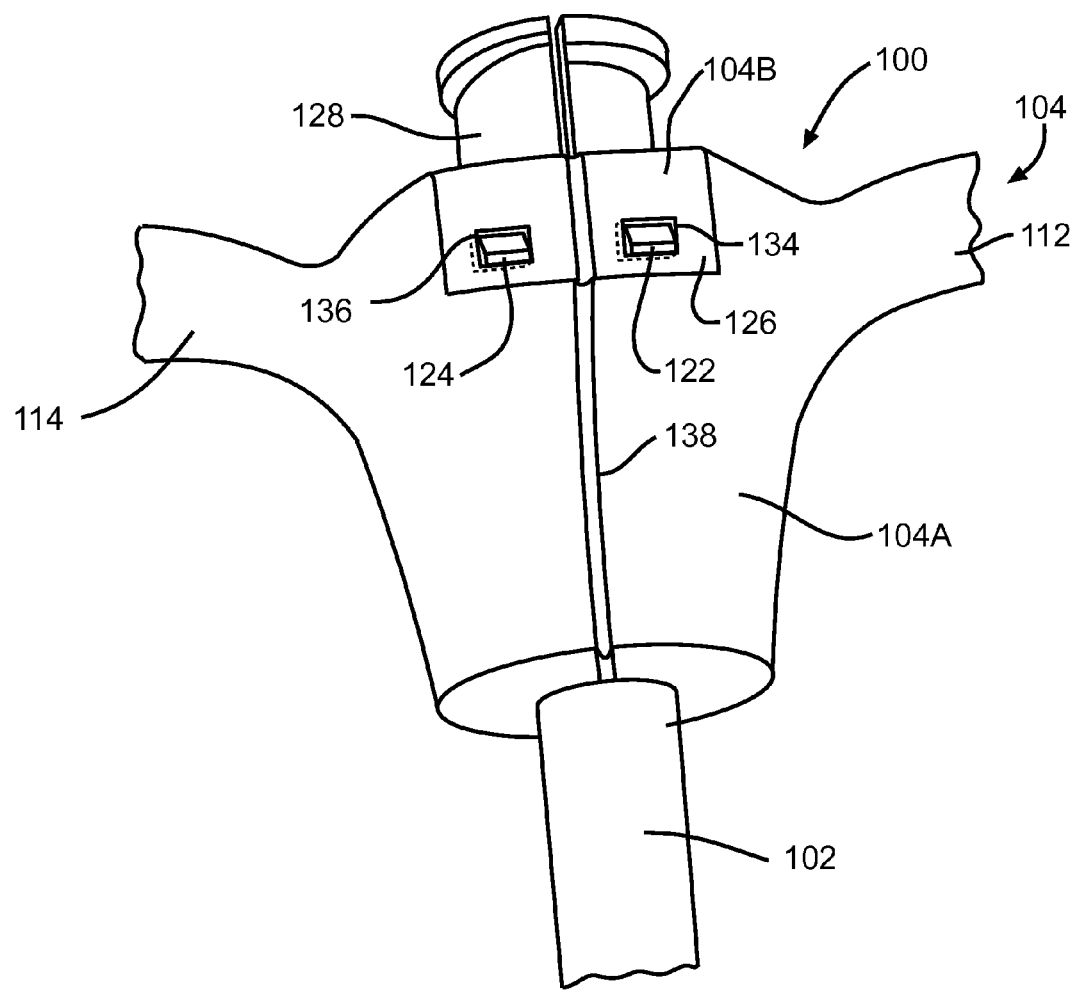
FIG. 4 is a perspective view, partly broken away, of the valved introducer assembly of the present invention shown in FIG.
Figure 4A:
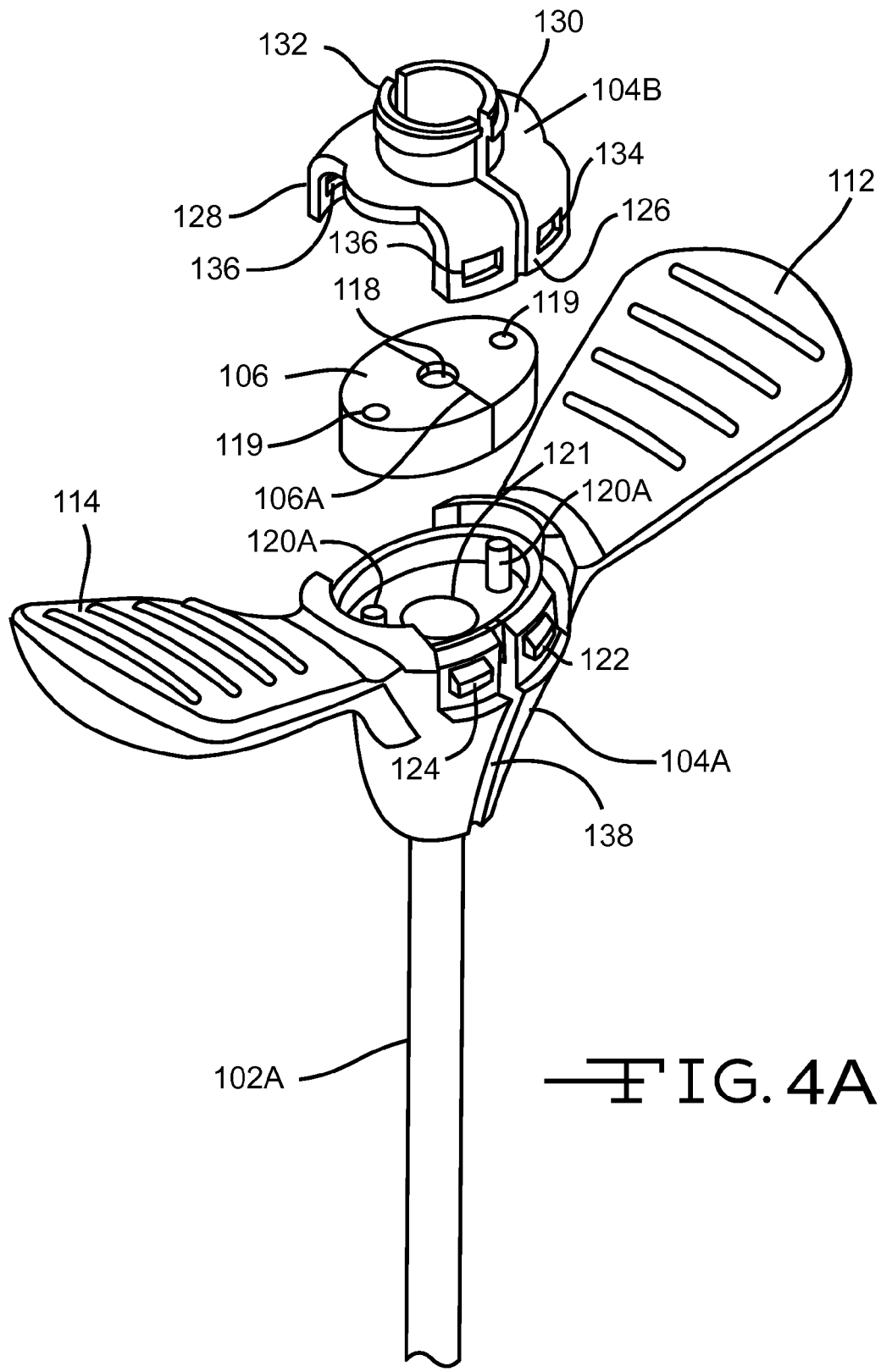
FIG. 4A is a partial exploded view of the valved introducer assembly 100 of the present invention.
Figure 5:
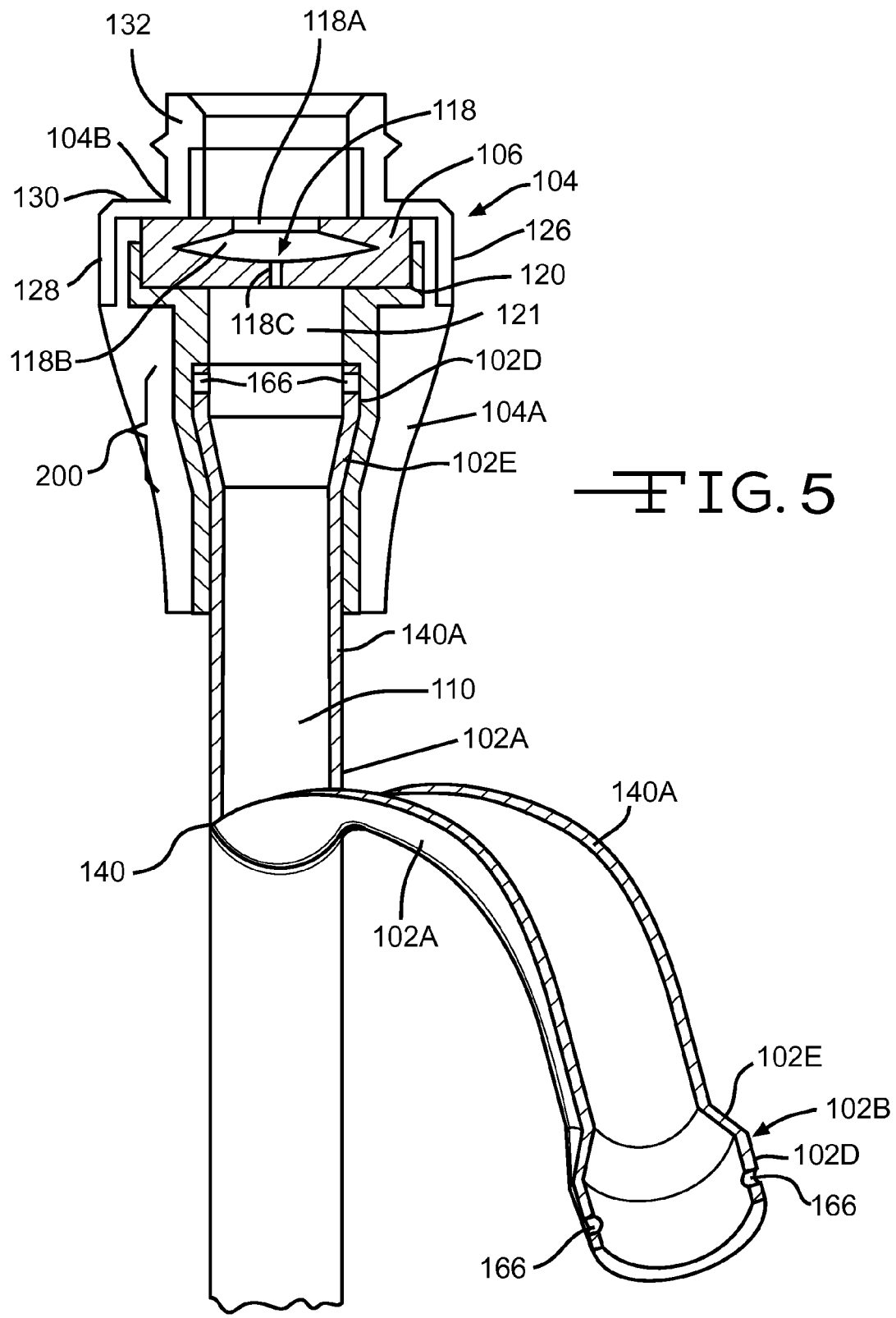
FIG. 5 is a side elevational view of the valved introducer assembly 10 of the present invention after the sheath 102 has been partially torn in half.

An annular ledge 120 is formed in the lower valve body 104A and provides a seat for the valve membrane 106. A pair of upstanding posts 120A resides on opposite sides of a through opening 121 in the lower valve body 104A. The posts 120A are received in the through holes 119 to help keep the valve membrane 106 seated on the annular ledge 120. The lower valve body 104A includes two pairs of side-by-side protrusions 122, 124 located on opposite sides of the body (only the protrusions on the front side are shown in FIG. 4).

The valve cap 104B comprises front and back sidewalls 126 and 128 depending from a central web 130. The web 130 supports an upstanding tube 132 that preferably provides a Leur-type fitting. The sidewalls 126, 128 include side-by-side windows 134, 136 sized to receive the protrusions 122, 124. The valve membrane 106 is then locked into position supported on the annular ledge 120 when the valve cap 1045 is snap attached to the lower valve body 104A with the protrusions 122, 124 received in the respective windows 134, 136. In that position, the central opening 118 of the valve membrane 106 is in axial alignment with the opening 121 in the lower valve body 104A and the longitudinal axis of the sheath lumen 110. The valve membrane opening 118 is a self-sealing structure that is sized to permit passage of the medical device such as the lead or catheter there through while sealing about the periphery thereof.

As is well known by those skilled in the art, a dilator (not shown) received inside the lumen 110 allows for the valved introducer assembly to be introduced into the vasculature of a patient, for instance, over a guide wire (not shown). This positions the distal end 102C of the sheath 102 inside the vasculature while the proximal section 102B and the valve assembly 104 remain outside the patient. After the introducer assembly 10 is inserted into a patient and the dilator has been removed from the sheath 102, other medical instruments can be easily inserted into and through the sheath 12 and introduced into the patient. All the while, the valve assembly 104 prevents blood and other body fluids from leaking out of the vasculature and outside air from getting in.

Then, once the lead or catheter is properly positioned in the vasculature, the valved introducer assembly 100 of the present invention is split apart for removal from the vasculature. This is done by holding the wings 112, 114 between the thumb and fore finger and counter rotating them with respect to each other while slowly moving the wings further apart. The valve housing 104 including the valve membrane 106 are readily separated. This occurs at a score line 138 running along the lower valve body 104A and the valve cap 104B including the Leur type fitting 132 and at the score line 106A in the valve membrane 106.

As the wings 112, 114 of the valve housing 104 are moved apart, the resulting halves of the valve housing begin to exert a force on the proximal section 102A of the sheath. These forces are sufficient to tear apart the relatively short web 168 located between the proximal end 102F of the cylindrical portion 102D and the perforation 166. The force generated by further manipulation of the wings 112, 114 is concentrated at the lower extent or distal stress point/area 166A of each perforation of the stress confining structure 200. This concentrated force is sufficient to cause the material of the cylindrical portion 102D distal of the perforation 166 to sever or tear apart. The sheath of the present invention is preferably of polytetrafluoroethylene (PTFE).

The preferred PTFE material for the sheath 102 has a unique molecular structure. Once a sufficient amount of force is exerted at the stress points 166A of the stress confining structure 200, the molecules comprising the cylindrical portion 102E of the proximal sheath section 102B begin to sever. Further pulling force causes the resulting tear 140 (FIG. 5) to propagate in a linear manner along the entire length of the sheath sidewall 102A to its distal end 102B. The tear 140 is extremely straight and parallel to the longitudinal axis 105 of the sheath 102. Importantly, the tear 140 is smooth and provides the physician with an even tactile feel that is a vast improvement over the saw-toothed tear afforded by the prior art Lee valved introducer 10.

Figure 2:
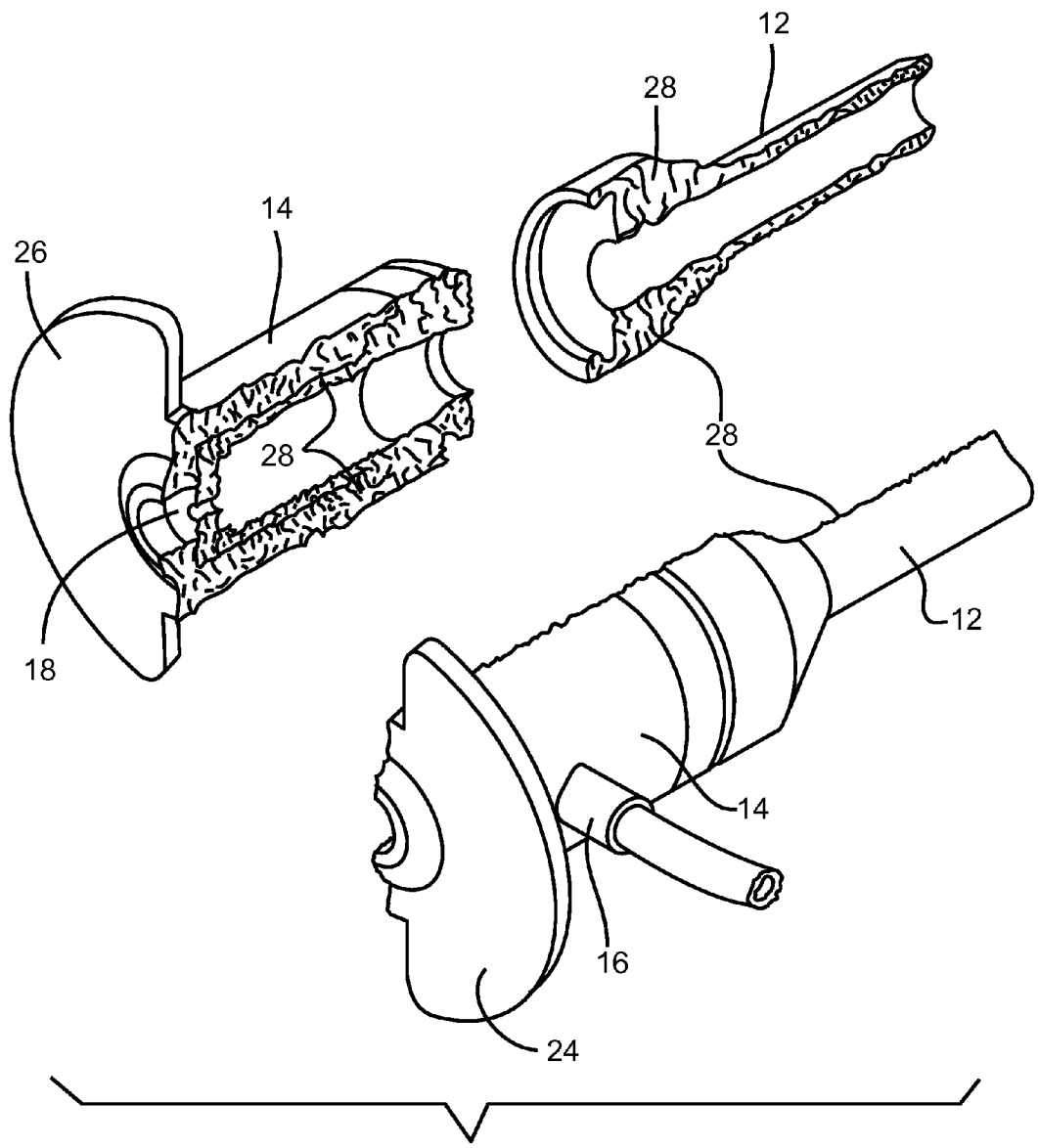
FIG. 2 is a perspective view of the prior art introducer apparatus 10 after having been separated into two halves along the score line 20 shown in FIG. 1.
Figure 3:
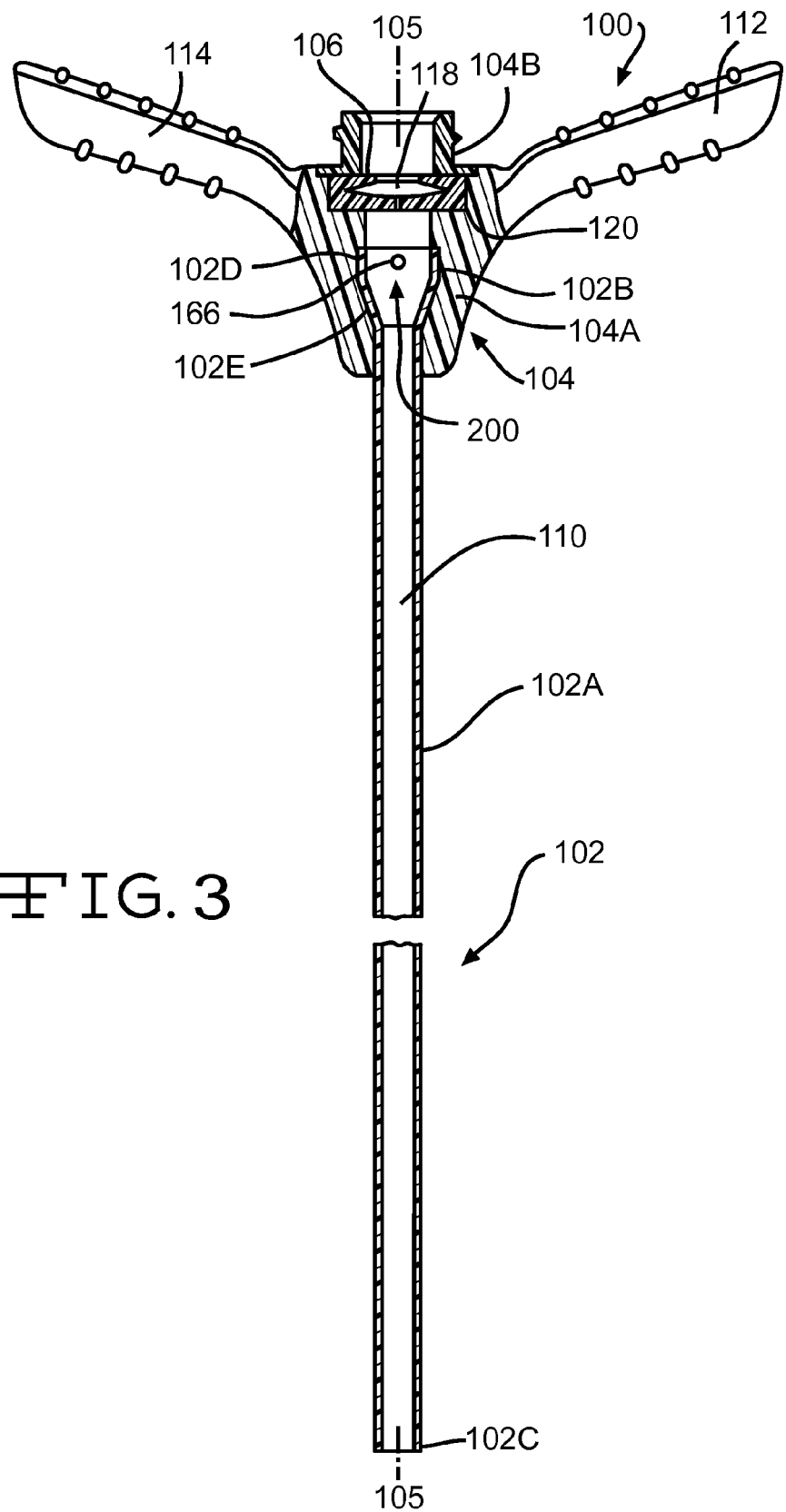
FIG. 3 is a front elevational view, partly in cross section, of a valved introducer assembly 100 according to the present invention.

In that respect, PTFE has a unique molecular structure that completely obviates the need for any scoring, weakening or mechanical alteration to facilitate precise, smooth and controllable splitting along the length of the sheath 102, thereby producing separated edges 140A after splitting that lack any perceptible "saw tooth" texture. The surfaces that are formed by splitting the sheath 102 made of PTFE, therefore, exhibit complete uniformity; they are devoid of localized variations in cross-sectional contour, thickness, surface annularity, or weakening by any means whatsoever. Further still, use of the PTFE material eliminates otherwise required steps in the manufacturing process of the prior art Lee introducer shown in FIGS. 1 and 2 that are potential opportunities for manufacturing errors and quality variations, such as improperly formed score lines, and the like, and that could potentially lead to product failures and patient endangerment.

While PTFE is the most preferred material for the sheath 102, other fluoropolymeric materials are also contemplated. These include polyhexafluoropropylene, tetrafluoroethylene-hexafluoropropylene copolymers, tetrafluoroethylene-perfluoroalkyl vinyl ether copolymers, polytrifluoroethylene, ethylene-tetrafluoroethylene copolymers, fluoroethylene-hydrocarbon vinyl ether copolymers, polychlorotrifluoroethylene, ethylene-chlorotrifluoroethylene copolymers, polyvinyl fluoride, polyvinylidene fluoride, vinylidene fluoride-hexafluoropropylene copolymers, fluorinated (meth)acrylate resins, 2-fluoroacrylate resins, fluorinated epoxy resins, fluorinated epoxy (meth)acrylate resins, fluorinated polyether resins, fluorinated polyimide resins, fluorinated polyester resins, fluorinated polyamide resins, fluorinated polycarbonate resins, fluorinated polyformal resins, fluorinated polyketone resins, fluorinated polyazomethine resins, fluorinated polyazole resins, and fluorinated polyallyloxysilane resins, vinylidene fluoride-hexafluoropropylene fluoroelastomer, vinylidene fluoride-tetrafluoroethylene fluoroelastomer, tetrafluoroethylene-perfluoroalkyl vinyl ether fluoroelastomer, vinylidene fluoride-tetrafluoroethylenehexafluoropropylene fluoroelastomer, vinylidene fluoride-tetrafluoroethylene-perfluoroalkyl vinyl ether fluoroelastomer, tetrafluoroethylene-perfluoroalkyl vinyl ether fluoroelastomer, propylene-tetrafluoroethylene fluoroelastomer, fluorosilicone rubber, fluorinated phosphazene rubber, fluorinated thermoplastic rubbers, and flexible fluorocarbon resins.

Another preferred embodiment of a stress confining structure 200 according to the present invention is illustrated in FIGS. 7 to 7B and comprises diametrically opposed V-shaped inlets 108. The V-shaped inlet 108 has a height designated as "L" in FIG. 7 measured from the proximal end 102F of the cylindrical portion 102D to the stress point 108A. The maximum width of the V-shaped inlet 108 at its mouth located at the proximal end 102F of the sheath is designated by the distance "M". The width N is measured as a straight line and not a circumferential distance between the two spaced apart locations 108B and can range from a maximum being the diameter of the cylindrical sheath portion 102D to a distance about 50% of that diameter. The height L is from about 5% to 300% of the distance M. More preferably, the height L is from about 50% to about 250% of the distance M.

As is the case with the previously described perforations 166, stresses initiated by manipulation of the wings 112, 114 are propagated to the point 108A of the V-shaped stress confining structure. Further manipulation of the wing structures 112, 114, causes the stresses to propagate the entire length of the sheath 102 to the distal end 102C thereof in a smooth and even tactile manner.

The present invention thus provides the proximal section 102B of the valved introducer 100 with structures that concentrate the tearing forces created by moving the wings 112, 114 apart to stress confining structures located diametrically opposite each other in the sheath sidewall 102A. The unique molecular properties of PTFE permit the separating forces concentrated at the stress point of the stress confining structures 200, such as circular perforations 166 or the V-shaped inlets 108, to propagate the entire length of the sheath. However, the present invention is not meant to be limited to the perforations 166 and V-shaped inlet 108. Any structure located at the proximal section 102B of the sheath that serves to concentrate the tearing forces to a confined area is contemplated by the scope of the present invention.

Alternate embodiments include the diametrically opposed V-shaped inlets 142 shown in FIG. 8 that are similar to the V-shaped inlets shown in FIG. 7, except that their troughs are somewhat radiused where the stress points 142A are formed.

FIG. 9 illustrates another embodiment of a stress confining structure for initiating a tearing separation of the sheath 102. The stress confining structure 200 is somewhat similar to the V-shaped inlets 108 shown in FIG. 7, but it is cut a significant distance into the length of the cylindrical portion 102D of the proximal sheath section 102B. This provides opposed upstanding webs 146 and 148 having a radius curvature. The transition between the webs 146, 148 and the V-shaped inlets 150 is somewhat squared off. The V-shaped inlets 150 provide stress points 150A that function in a similar manner as stress points 108A.

FIG. 10 shows another embodiment of V-shaped inlets 152 that is similar to inlets 150. However, the transition between the webs 154, 156 and the V-shaped inlets 152 is rounded-off.

In the embodiment illustrated in FIG. 11, diamond-shaped openings 158 are provided at diametrical locations on the cylindrical portion 102D of the proximal sheath section 102S. With this structure, similar to the circular perforation in FIG. 6, the tearing force exerted against the proximal section 102B must be sufficient to break through the relatively small length of material or web indicated by numerical designation 160. Then, the tearing forces are concentrated at the stress points 158A of the diamond-shaped openings.

FIG. 12 illustrates another embodiment of a stress confining structure 200 for initiating a tearing separation of the sheath 102. The stress confining structure is a radius cut-out 162 extending about halfway around the circumference of the cylindrical portion 102D of the proximal sheath section 102B. This creates diametrically opposed stress points 162 located at the step 164 between the cut-out 162 and the cylindrical portion 102D of the proximal sheath section 102B.

FIG. 13 illustrates another embodiment of a stress confining structure comprising opposed radiused troughs 170.

FIG. 14 is similar except the radiused troughs 172 begin some distance into the length of the cylindrical portion 102D of the proximal sheath section 102A. This forms radiused webs 174, 176, each having opposed planer sides (only the planar sides 174A, 176A leading to the front radiused trough 172 are provided with numerical designations). In both structures, the tearing forces are directed to the respective stress areas 170A, 172A at the bottom of the troughs 170, 172 and the tear propagates from there along the entire length of the sheath to its distal end 102C.

FIG. 15 illustrates another embodiment of stress confining structure comprising radiused troughs 178 similar to those shown in FIGS. 13 and 14, but leading to a circular inlets 180. In FIG. 16, the radiused troughs 182 lead to diamond-shaped inlets 184. In both structures, the tearing forces are directed to the stress areas 180A or 184A at the bottom of the respective circular inlets 180 or the V-shaped inlets 184. The tear propagates from there the entire length of the sheath 102 to its distal end 102C.

FIG. 17 illustrates another embodiment of a stress confining structure comprising diametrically opposed V-shaped inlets 186 leading to circular inlets 188. In this case, the tearing forces are directed to the stress areas 188A at the bottom of the circular inlets 188. The tear propagates from there the entire length of the sheath to its distal end 102B.

Thus, the present invention has described several structures suitable for as stress confining structures for concentrating the separating forces exerted at the proximal section 102B of the sheath 102 by a pulling manipulation of the wings 112, 114. In each structure, the total forces imparted to the wings 112, 114 are concentrated at either diametrically opposed points 108A, 142A, 150A, 152A, 158A, 162A, 166A, 170A, 172A, 180A, 182A and 186A. Together with the unique molecular properties afforded by PTFE as the preferred material for the sheath 102, once a tear begins it propagates the entire length of the sheath, no matter how long, in an extremely smooth manner that provided the physician with a very desirable tactile feel.

It is, therefore, apparent that there has been provided, in accordance with the present invention, an introducer assembly comprising a valve housing supported on the proximal end of a PTFE sheath having a novel structure for removal from the venous system of a patient. While this invention has been described in conjunction with preferred embodiments thereof, it is evident that many alternatives, modifications, and variations will be apparent to those skilled in the art. Accordingly, it is intended to embrace all such alternatives, modifications and variations that fall within the broad scope of the appended claims.

What is claimed is:

1. A valve introducer assembly for inserting a medical device into a patient, the introducer assembly comprising:
    a) a sheath comprising a sheath sidewall defining a sheath lumen having a length extending from a proximal end of a proximal sheath portion to a sheath distal end;
    b) a valve assembly comprising a valve housing secured to the proximal sheath portion, wherein the valve housing supports a valve membrane that provides for passage of a medical device through the valve assembly and sheath lumen while preventing body fluids or ambient air from leaking into or out of the valve assembly; and
    c) at least one stress confining structure comprising at least two diametrically opposed perforations extending completely through a thickness of the sheath sidewall at the proximal sheath portion housed inside the valve housing, wherein the stress confining perforations are spaced from the proximal sheath end by a web of sheath material and unoccupied by a valve material comprising the valve housing.

2. The valve introducer assembly of claim 1 wherein a shape of the stress confining perforations is selected from the group consisting of a circle, a diamond, a triangular, an oblong, a star, and combinations thereof.

3. The valve introducer assembly of claim 1 wherein the proximal sheath portion includes a plurality of second perforations spaced about the circumference thereof and located more distally from the proximal sheath end than the opposed stress confining perforations and wherein the second perforations facilitate securing the valve assembly to the sheath.

4. The valve introducer of claim 3 wherein the second perforations are of a shape selected from the group consisting of a circle, a diamond, a triangular, an oblong, a star, and combinations thereof.

5. The valve introducer assembly of claim 1 wherein the valve housing has at least two opposing wings which facilitate manipulation to initiate a tear along the length of the sheath beginning at the opposed webs and stress confining perforations.

6. The valve introducer assembly of claim 1 wherein the proximal sheath portion is of a first diameter that meets a frusto-conical transition extending distally and inwardly to a second, lesser diameter housed in the valve housing.

7. The valve introducer assembly of claim 1 wherein the sheath is composed of a fluoropolymeric material selected from the group consisting of PTFE, polyhexafluoropropylene, tetrafluoroethylene-hexafluoropropylene copolymers, tetrafluoroethylene-perfluoroalkyl vinyl ether copolymers, polytrifluoroethylene, ethylene-tetrafluoroethylene copolymers, fluoroethylene-hydrocarbon vinyl ether copolymers, polychlorotrifluoroethylene, ethylene-chlorotrifluoroethylene copolymers, polyvinyl fluoride, polyvinylidene fluoride, vinylidene fluoride-hexafluoropropylene copolymers, fluorinated (meth)acrylate resins, 2-fluoroacrylate resins, fluorinated epoxy resins, fluorinated epoxy (meth)acrylate resins, fluorinated polyether resins, fluorinated polyimide resins, fluorinated polyester resins, fluorinated polyamide resins, fluorinated polycarbonate resins, fluorinated polyformal resins, fluorinated polyketone resins, fluorinated polyazomethine resins, fluorinated polyazole resins, and fluorinated polyallyloxysilane resins, vinylidene fluoride-hexafluoropropylene fluoroelastomer, vinylidene fluoride-tetrafluoroethylene fluoroelastomer, tetrafluoroethylene-perfluoroalkyl vinyl ether fluoroelastomer, vinylidene fluoride-tetrafluoroethylenehexafluoropropylene fluoroelastomer, vinylidene fluoride-tetrafluoroethylene-perfluoroalkyl vinyl ether fluoroelastomer, tetrafluoroethylene-perfluoroalkyl vinyl ether fluoroelastomer, propylene-tetrafluoroethylene fluoroelastomer, fluorosilicone rubber, fluorinated phosphazene rubber, fluorinated thermoplastic rubbers, and flexible fluorocarbon resins.

8. The valve introducer assembly of claim 1 wherein the stress confining perforations have a diameter ranging from about 0.01 inches to about 0.10 inches.

9. The valve introducer assembly of claim 1 wherein the web is spaced from about 0.01 inches to about 0.05 inches from the proximal end of the sheath.

10. A valve introducer assembly for inserting a medical device into a patient, the introducer assembly comprising:
    a) a sheath comprising a sheath sidewall defining a sheath lumen having a length extending from a proximal end of a proximal sheath portion to a sheath distal end;

b) a valve assembly comprising a valve housing secured to the proximal sheath portion, wherein the valve housing supports a valve membrane that provides for passage of a medical device through the valve assembly and sheath lumen while preventing body fluids or ambient air from leaking into or out of the valve assembly, wherein the valve housing has at least two opposing wings which facilitate manipulation to initiate a tear along the length of the sheath; and c) at least one stress confining structure comprising at least two diametrically opposed circular perforations extending completely through a thickness of the sheath sidewall at the proximal sheath portion housed inside the valve housing, wherein the stress confining perforations are spaced from the proximal sheath end by a web of sheath material and unoccupied by a valve material comprising the valve housing.

11. The valve introducer assembly of claim 10 wherein the stress confining perforations have a diameter ranging from about 0.01 inches to about 0.10 inches.

12. The valve introducer assembly of claim 10 wherein the web is spaced from about 0.01 inches to about 0.05 inches from the proximal end of the sheath.

13. A method of inserting a medical device into a patient, the method comprising the steps of:

a) providing a valve introducer assembly comprised of a sheath supporting a valve assembly, the sheath comprising a sheath sidewall defining a sheath lumen having a length extending from a proximal end of a proximal sheath portion to a sheath distal end with at least one stress confining structure comprising at least two diametrically opposed perforations extending completely through a thickness of the sheath sidewall at the proximal sheath portion housed inside the valve housing, wherein the stress confining perforations are spaced from the proximal sheath end by a web of sheath material and unoccupied by a valve material comprising the valve housing;

b) inserting the valve introducer assembly into a patient so that a distal portion of the sheath resides in a vasculature and the proximal sheath portion including the valve assembly is outside the vasculature;

c) inserting a medical device through the valve introducer assembly and into the vasculature;

d) splitting the valve introducer assembly apart by manipulating opposed wings supported by the valve housing to thereby break the valve assembly and initiate a tear along the length of the sheath beginning at the opposed webs and continuing through the stress confining perforations and then along the remainder of the length of the sheath so that the valve assembly and sheath separate into substantially identical half portions; and e) removing the half portions of the valve introducer assembly from the patient.

14. The method of claim 13 including providing the stress confining perforations having a diameter ranging from about 0.01 inches to about 0.10 inches.

15. The method of claim 13 including providing the web being spaced from about 0.01 inches to about 0.05 inches from the proximal end of the sheath.

* * * * *